United States Patent
Aoyama et al.

(12) 
(10) Patent No.: US 6,255,524 B1
(45) Date of Patent: Jul. 3, 2001

(54) PROCESS FOR PRODUCING ACID CHLORIDES HAVING POLYFLUOROALKYL GROUPS

(75) Inventors: Hirokazu Aoyama; Shoji Takagi; Shinichi Matsumura; Yoshinori Tanaka, all of Settsu (JP)

(73) Assignee: Daikin Industries Ltd., Osaka (JP)

( * ) Notice: Subject to any disclaimer, the term of this patent is extended or adjusted under 35 U.S.C. 154(b) by 0 days.

(21) Appl. No.: 09/331,785

(22) PCT Filed: Dec. 3, 1997

(86) PCT No.: PCT/JP97/04412

§ 371 Date: Jun. 25, 1999

§ 102(e) Date: Jun. 25, 1999

(87) PCT Pub. No.: WO98/29377

PCT Pub. Date: Jul. 9, 1998

(30) Foreign Application Priority Data

Dec. 25, 1996 (JP) ..................................................... 8-345083

(51) Int. Cl.$^7$ .............................. C07C 69/63; C07C 51/58
(52) U.S. Cl. .............................................. 560/227; 562/863
(58) Field of Search ............................... 560/227; 562/863

(56) References Cited

U.S. PATENT DOCUMENTS 4,124,469 11/1978 Bathelt .
4,643,851 2/1987 Cheminal et al. .

FOREIGN PATENT DOCUMENTS

| 1509110 | * 4/1978 | (GB) . |
|---|---|---|
| 59-98031 | 6/1984 | (JP) . |
| 61-33014 | 7/1986 | (JP) . |
| 61-33014B2 | 7/1986 | (JP) . |

OTHER PUBLICATIONS

Kamigata K. et al. Journal of the Chemical Society, No. 3, pp. 627–633, (Mar. 1991).

Nobumasa Kamigata et al., J. Chem. Soc., Perkin Trans. 1 (1991), (3), p. 627–633.

\* cited by examiner

*Primary Examiner*—Paul J. Killos
(74) *Attorney, Agent, or Firm*—Birch, Stewart, Kolasch & Birch, LLP

(57) ABSTRACT

An acid chloride can be produced at a high yield from a primary alcohol having a polyfluoroalkyl group and one methylene group by (1) a method in which $R_fCH_2OH$ (wherein $R_f$ is a polyfluoroalkyl group) is reacted with chlorine to produce $R_fCOCl$, (2) a method in which $R_fCHO$ is reacted with chlorine to produce $R_fCOCl$, and (3) a method for producing an acid chloride comprising (a) a step in which an aldehyde ($R_fCHO$) is formed from an alcohol ($R_fCH_2OH$), (b) a step in which a monochloroester ($R_fCOOCHClR_f$) is formed from the aldehyde and an acid chloride ($R_fCOCl$), and (c) a step in which the acid chloride ($R_fCOCl$) is formed from the monochloroester.

5 Claims, 1 Drawing Sheet

PROCESS FOR PRODUCING ACID CHLORIDES HAVING POLYFLUOROALKYL GROUPS

This application is the national phase under 35 U.S.C. §371 of PCT International Application No. PCT/JP97/04412 which has an International filing date of Dec. 3, 1997 which designated the United States of America.

FIELD OF THE INVENTION

The present invention relates to a method for producing an acid chloride having a polyfluoroalkyl group.

RELATED ART

As a method for producing an acid chloride from a primary alcohol having a polyfluoroalkyl group and two methylene groups ($R_fCH_2CH_2OH$, wherein $R_f$ is a polyfluoroalkyl group), a method via chlorination by means of light has been proposed (Japanese Patent Application Kokoku Publication No. 033014/1986).

When a primary alcohol having a polyfluoroalkyl group and one methylene group ($R_fCH_2OH$, wherein $R_f$ is a polyfluoroalkyl group) is chlorinated by means of light, however, it is difficult to give an acid chloride at a good yield, because the acid chloride formed reacts with the alcohol to give an ester as a by-product.

SUMMARY OF THE INVENTION

An object of the present invention is to provide a method for industrially producing an acid chloride ($R_fCOCl$) from a primary alcohol having a polyfluoroalkyl group and one methylene group ($R_fCH_2OH$) at a high yield.

The present invention provides a method for producing an aldehyde represented by the formula:

$$R_fCHO$$

wherein $R_f$ is a polyfluoroalkyl group, the method comprising reacting a primary alcohol represented by the formula:

$$R_fCH_2OH$$

wherein $R_f$ is a polyfluoroalkyl group,
with chlorine in the presence of a catalyst.

The present invention provides a method for producing an acid chloride represented by the formula:

$$R_fCOCl$$

wherein $R_f$ is a polyfluoroalkyl group, the method comprising reacting an aldehyde represented by the formula:

$$R_fCHO$$

wherein $R_f$ is a polyfluoroalkyl group, with chlorine in the presence of a catalyst.

The present invention provides a method for producing an acid chloride represented by the formula:

$$R_fCOCl$$

wherein $R_f$ is a polyfluoroalkyl group,
the method comprising reacting a primary alcohol represented by the formula:

$$R_fCH_2OH$$

wherein $R_f$ is a polyfluoroalkyl group,
with chlorine in the presence of a catalyst.

The present invention provides a method for producing an acid chloride represented by the formula:

$$R_fCOCl$$

wherein $R_f$ is a polyfluoroalkyl group,
the method comprising reacting a primary alcohol represented by the formula:

$$RCH_2OH$$

wherein $R_f$ is a polyfluoroalkyl group,
with chlorine in the presence of a catalyst to give an aldehyde represented by the formula:

$$R_fCHO$$

wherein $R_f$ is a polyfluoroalkyl group, and then reacting the aldehyde with chlorine in the presence of a catalyst to give the acid chloride.

The present invention provides a method for producing a monochloroester represented by the formula:

$$R_fCOOCHClR_f$$

wherein $R_f$ is a polyfluoroalkyl group,
the method comprising reacting an aldehyde represented by the formula:

$$R_fCHO$$

wherein $R_f$ is a polyfluoroalkyl group,
with an acid chloride represented by the formula:

$$R_fCOCl$$

wherein $R_f$ is a polyfluoroalkyl group,
in the presence of a catalyst.

The present invention provides a method for producing an acid chloride represented by the formula:

$$R_fCOCl$$

wherein $R_f$ is a polyfluoroalkyl group,
the method comprising reacting a monochloroester represented by the formula:

$$R_fCOOCHClR_f$$

wherein $R_f$ is a polyfluoroalkyl group,
with chlorine in the presence of a catalyst.

The present invention provides a method for producing an acid chloride represented by the formula:

$$R_fCOCl$$

wherein $R_f$ is a polyfluoroalkyl group,
the method comprising:

(a) a step of reacting a primary alcohol represented by the formula:

$$R_fCH_2OH$$

wherein $R_f$ is a polyfluoroalkyl group
with chlorine in the presence of a catalyst to give an aldehyde represented by the formula:

$$R_fCHO$$

wherein $R_f$ is a polyfluoroalkyl group;

(b) a step of reacting the aldehyde with an acid chloride represented by the formula:

$$R_fCOCl$$

wherein $R_f$ is a polyfluoroalkyl group,
in the presence of a catalyst to give a monochloroester represented by the formula:

$$R_fCOOCHClR_f$$

wherein $R_f$ is a polyfluoroalkyl group; and
(c) a step of reacting the monochloroester with chlorine in the presence of a catalyst to give the acid chloride.

The present invention provides a method for producing an acid chloride represented by the formula:

$$R_fCOCl$$

wherein $R_f$ is a polyfluoroalkyl group,
the method comprising:
(a) a step of obtaining an aldehyde having the $R_f$ group by reacting an alcohol represented by the formula:

$$R_fCH_2OH$$

wherein $R_f$ is a polyfluoroalkyl group,
with chlorine in the presence of a catalyst to give the aldehyde represented by the formula:

$$R_fCHO$$

wherein $R_f$ is a polyfluoroalkyl group,
in which step the alcohol is brought to reflux in a first reactor filled with the catalyst, and is reacted with chlorine supplied continuously, and the aldehyde formed is removed from a column top of the first reactor;
(b) a step of obtaining a monochloroester represented by the formula:

$$R_fCOOCHClR_f$$

wherein $R_f$ is a polyfluoroalkyl group,
by reacting the aldehyde, in the presence of a catalyst, with an acid chloride represented by the formula:

$$R_fCOCl$$

wherein $R_f$ is a polyfluoroalkyl group,
in which step the aldehyde and the acid chloride in their liquid states are introduced in parallel flow into a second reactor filled with the catalyst, and the monochloroester is removed in its liquid state;
(c) a step of obtaining the acid chloride by reacting the monochloroester with chlorine in the presence of a catalyst, in which step the monochloroester in its liquid state and chlorine are introduced in parallel flow or in counterflow into a third reactor filled with the catalyst, and a mixture comprising the acid chloride and the aldehyde is removed in its gas state; and
(d) a step of eliminating the aldehyde from the mixture comprising the aldehyde and the acid chloride, in which aldehyde-eliminating step the mixture liquid comprising the aldehyde and the acid chloride is introduced into a fourth reactor filled with a catalyst, and the acid chloride is removed in its liquid state.

The present invention provides a monochloroester represented by the formula:

$$H(CF_2)_6COOCHCl(CF_2)_6H$$

DETAILED DESCRIPTION OF THE INVENTION

Figure 1:
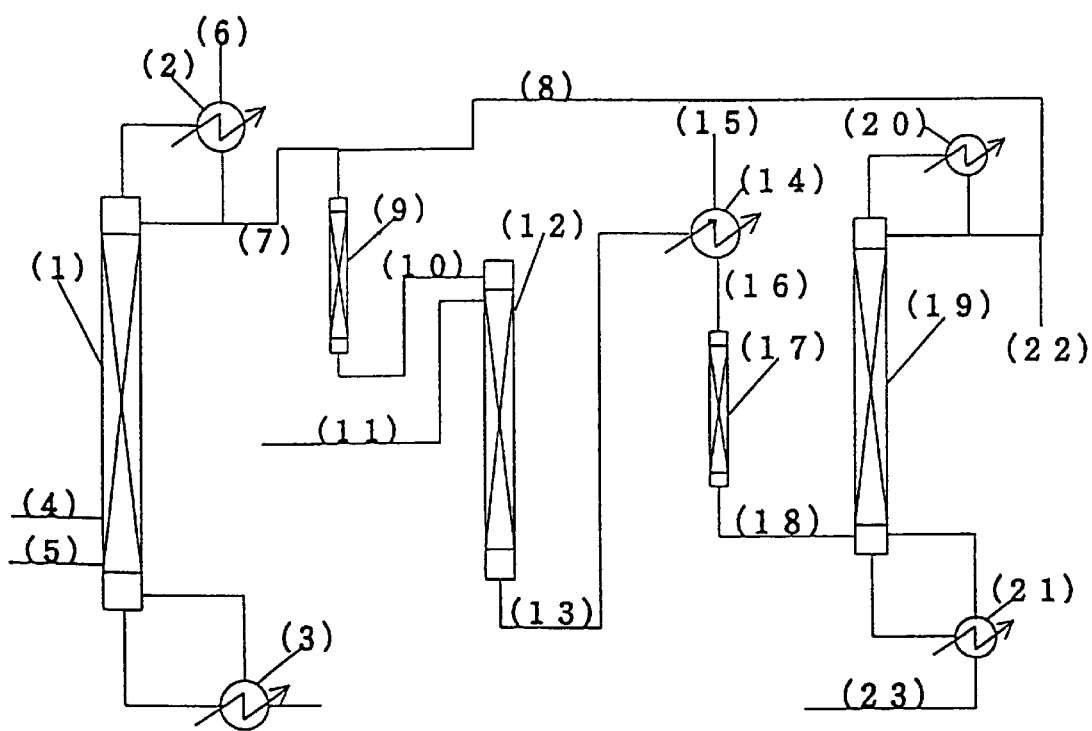
FIG. 1 is a flow sheet of a method according to the present invention.

Examples of the primary alcohol used in the present invention include linear compounds having a primary hydroxyl group represented by the general formula (I):

$$X(CF_2)_nCH_2OH \qquad (I)$$

wherein X is F, Cl, or H, and n is a number from 1 to 20. The primary alcohol is preferably $F(CF_2)_nCH_2OH$ or $H(CF_2)_nCH_2OH$. The number "n" is preferably from 1 to 10, and particularly from 4 to 8. Specific examples of the preferred primary alcohol are 2,2,3,3,4,4,5,5-octafluoropentanol [$H(CF_2)_4CH_2OH$], 2,2,3,3,4,4,5,5,5-nonafluoropentanol [$F(CF_2)_4CH_2OH$], 2,2,3,3,3-pentafluoropropanol ($CF_3CF_2CH_2OH$), 2,2,3,3,4,4,5,5,6,6,7,7-dodecafluoroheptanol [$H(CF_2)_6CH_2OH$], 2,2,3,3,4,4,5,5,6,6,7,7,7-tridecafluoroheptanol [$F(CF_2)_6CH_2OH$], 2,2,3,3,4,4,5,5,6,6,7,7,8,8,9,9-hexadecafluorononanol [$H(CF_2)_8CH_2OH$], and 2,2,3,3,4,4,5,5,6,6,7,7,8,8,9,9-heptadecafluorononanol [$F(CF_2)_8CH_2OH$].

In the present invention, the catalyst is preferably activated carbon. Any types of activated carbon can work effectively, including those derived from, for example, coconut husk-, coal-, or wood-based raw materials, in the form of pellet, crushed, granule, sphere, powder or the like, and for use in decoloring liquid phases, in purifying, separating or recovering gases, for use as a catalyst or a catalyst support, or for use in preventing water pollution, air pollution or other environmental pollution. Preferably, the activated carbon has a particle size of 4–12 mesh and is in the form of pellet or particle. Specific examples of the catalyst include particulate Sirasagi G2X or S2X commercially available from Takeda Chemical Industries, Ltd., and Kureha bead activated carbon LLP commercially available from Kureha Chemical Industry Co., Ltd. In the present invention, the catalyst dose not experience any decrease in its catalytic effect and can be used on a semipermanent basis, eliminating the necessity for catalyst exchange.

The reaction mode may be either a liquid phase reaction or a gas phase reaction. The liquids or gases may contact with each other either in counterflow or in parallel flow. The reaction may be conducted under increased, normal, or reduced pressure.

The acid chloride can be produced by reacting the alcohol with chlorine in the presence of a catalyst.

$$R_fCH_2OH + 2Cl_2 \rightarrow R_fCOCl + 3HCl$$

The amount of chlorine used is preferably in the range of 0.1–10 moles, more preferably in the range of 0.5–5 moles, per one mole of the alcohol. The reaction temperature is preferably in the range of 50° C.–300° C., more preferably in the range of 100° C.–200° C.

The reaction between the alcohol and chlorine may be conducted in a gas phase mode or a liquid-irrigation packed column mode. In the case of a gas phase reaction, the reaction pressure is preferably in the range from −1.0 kg/cm²G to 5 kg/cm²G, more preferably in the range from 0 kg/cm²G to 3 kg/cm²G.

The contact time W/Fo (on a gas basis) is preferably in the range of 10–1000, more preferably in the range of 50–500 g.sec/cc, wherein W is the weight of the catalyst (in grams) and Fo is the total flow rate of the alcohol and chlorine (in cc/sec).

When the aldehyde, which is the intermediate before the acid chloride is formed, is separated from the alcohol and the aldehyde alone is reacted with chlorine to give the acid chloride, a remarkable increase in yield can be observed in comparison with the case where the acid chloride is produced from the alcohol.

The acid chloride can also be produced by reacting the aldehyde with chlorine in the presence of a catalyst.

$$R_fCHO+Cl_2 \rightarrow R_fCOCl+HCl$$

The amount of chlorine used is preferably in the range of 0.1–10 moles, more preferably in the range of 0.5–5 moles, per one mole of the aldehyde. The reaction temperature is preferably in the range of 80° C.–250° C., more preferably in the range of 130° C.–200° C.

The reaction between the aldehyde and chlorine can be conducted in a liquid-irrigation packed column reaction mode. The contact time W/Fo (on a gas basis) is preferably in the range of 10–1,000, more preferably in the range of 50–500 g.sec/cc, wherein W is the weight of the catalyst (in grams) and Fo is the total flow rate of the aldehyde and chlorine (in cc/sec).

The aldehyde can also be produced, for example, by reacting the alcohol ($R_fCH_2OH$) with chlorine.

In addition, a further increase in yield of the acid chloride may be achieved by using the monochloroester, which is generated from the aldehyde ($R_fCHO$) and the acid chloride ($R_fCOCl$), as an intermediate substance.

Accordingly, a method of the present invention preferably comprises (a) a step in which the aldehyde is generated from the alcohol and chlorine, (b) a step in which the monochloroester is generated from the aldehyde and the acid chloride, and (c) a step in which the acid chloride is generated from the monochloroester and chlorine.

(a) Aldehyde Formation $$R_fCH_2OH+Cl_2 \rightarrow R_fCHO+2HCl$$

The amount of chlorine used is preferably in the range of 0.001–2 moles, more preferably in the range of 0.01–1 mole, especially preferably in the range of 0.05–0.5 mole, for example, 0.01–0.3 mole, per one mole of the alcohol. The reaction temperature is preferably in the range of 100° C.–300° C., more preferably in the range of 150° C.–200° C. The reaction can be conducted in a continuous mode.

It is preferred to conduct the reaction in a distillation reaction mode. The reaction pressure is preferably in the range from reduced pressure (for example, 1 mmHg) to 5 kg/cm²G, more preferably in the range of 0–3 kg/cm²G.

The contact time W/F (on a gas basis) is preferably in the range of 10–1,000 g.sec/cc, more preferably in the range of 50–500 g.sec/cc, wherein W is the weight of the catalyst (in grams) and F is the total flow rate of the alcohol and chlorine (in cc/sec).

(b) Monochloroester Formation $$R_fCHO+R_fCOCl \rightarrow R_fCOOCHClR_f$$

The amount of the acid chloride used is preferably in the range of 0.3–3.0 moles, more preferably in the range of 1.0–2.0 moles, per one mole of the aldehyde. The reaction temperature is preferably in the range of 20° C.–200° C., more preferably in the range of 80° C.–140° C. The reaction can be conducted in a continuous mode.

It is preferred to conduct the reaction in a liquid phase. The contact time W/Fo (on a liquid basis) is preferably in the range of 10–10,000, more preferably in the range of 100–10,000 g.sec/cc, especially preferably in the range of 500–5000 g.sec/cc, wherein W is the weight of the catalyst (in grams) and Fo is the total flow rate of the aldehyde and the acid chloride (in cc/sec).

(c) Acid Chloride Formation $$R_fCOOCHClR_f+Cl_2 \rightarrow 2R_fCOCl+HCl$$

The amount of chlorine used is preferably in the range of 0.1–5 moles, more preferably in the range of 1–3 moles, especially preferably in the range of 1–2 moles, per one mole of the monochloroester. The reaction temperature is preferably in the range of 80–250° C., more preferably in the range of 120° C.–200° C., especially preferably in the range of 130–180° C. The reaction can be conducted in a continuous mode.

A preferred reaction mode for the acid chloride formation is a liquid-irrigation packed column reaction mode. The contact time W/Fo (on a liquid basis) is preferably in the range of 1,000–10,000 g.sec/cc, more preferably in the range of 5,000–50,000 g.sec/cc, wherein W is the weight of the catalyst (in grams) and Fo is the total flow rate of the monochloroester and chlorine (in cc/sec).

The reaction in which an alcohol having the $R_f$ group is chlorinated in the presence of a catalyst to synthesize an acid chloride having the $R_f$ group is a consecutive reaction proceeding in two steps from the alcohol to the aldehyde and then to the acid chloride, and both of the reaction steps are highly exothermic. The conduction in a gas phase may cause the generation of hot spots within the reactor, which makes it difficult to control the reaction temperature, and in some cases, the increase in temperature may cause problems such as decrease in yield due to increased by-products, enhanced deterioration of the catalyst, and accelerated corrosion of the reactor. As one of methods for solving these problems, a multi-tubular reactor may be used to achieve a steady control of the reaction temperature. The use of multi-tubular reactor, however, causes other problems of increases in equipment costs and in number of steps for loading and unloading the catalyst.

Under the circumstances, the present invention overcomes the problems as described above encountered in producing an acid chloride having the $R_f$ group from an alcohol having the $R_f$ group as a starting material, and thereby provides a method for producing the same efficiently and industrially at a low cost.

According to the present invention, in the method for producing an acid chloride having the $R_f$ group from an alcohol having the $R_f$ group as a starting material, 1. the alcohol is reacted with chlorine in a first reactor (also referred to as a distillation reactor) in the presence of a catalyst to produce an aldehyde;
2. the aldehyde formed is reacted in a second reactor (also referred to as a pre-reactor) with the acid chloride, which is the final product, in the presence of a catalyst to produce a monochloroester;
3. the monochloroester formed is reacted with chlorine in a third reactor (also referred to as a main reactor) in the presence of a catalyst to produce the acid chloride;
4. the acid chloride formed is further reacted in a fourth reactor (referred to as an after-reactor) to convert the aldehyde remaining in the acid chloride in a small amount to the monochloroester, and thereby reduce the aldehyde concentration; and
5. the acid chloride is purified in a rectifying column to give the high purity acid chloride as the final product, while a part of the acid chloride is recycled for the monochloroester formation.

The present invention is described below with reference to a flow sheet shown in FIG. 1.

Raw materials, an alcohol (5) and chlorine (4), are introduced into a first reactor (1) in the rectifying operational status, reacted with each other in the presence of a catalyst, and the aldehyde in its liquid state is removed from a column top. The reason why the first reaction is distillation type is that the chlorine concentration is kept low (for example, at 1–2 mol %) at each part of the reactor by circulating the organic compound in a larger quantity relative to the amount of chlorine supplied, and thereby the reaction rate is controlled to reduce the amount of generated heat, and also that the generation of hot spots is prevented by absorbing the generated heat as the vaporization heat of a large amount of the reflux liquid. The reflux ratio required for this end is preferably in the range of 0.5–100, more preferably in the range of 1–50 (for example, 25). The first reactor (1) is equipped with a condenser (2) and a reboiler (3). The reaction liquid (7) is removed from the column top of the reactor (1). Uncondensed gases (6) are removed from the condenser (2).

The position and proportion of the catalyst-filled bed in the first reactor are important. If whole of the first reactor is completely filled with the catalyst, the aldehyde concentrated at the upper part of the reactor by the rectification effect may react with chlorine to form an acid chloride, which in turn reacts immediately with the alcohol to form an ester as an impurity, resulting in possible decrease in yield of the aldehyde, and therefore of the acid chloride. Accordingly, only the lower part of the first reactor is charged with the catalyst, while the upper part of the first reactor is charged with a usual filler (for example, ball rings). Regarding the packing ratio between the catalyst and the filler, the catalyst is filled at the height of preferably $1/3$–$3/4$, more preferably $1/2$–$2/3$, of the overall height of the packed bed.

Although hydrochloric acid formed in the first reactor and unreacted chlorine are removed from the column top in their gas states, the aldehyde removed from the column top in its liquid state is also contaminated with hydrochloric acid and chlorine to some extent. There is no need to remove the contaminating hydrochloric acid and chlorine, since they have no effects on the subsequent reactions.

Then, the aldehyde formed in the first reactor and the acid chloride which is the objective compound in the present invention are introduced into a second reactor (9), and reacted with each other in the presence of a catalyst to form the monochloroester. The acid chloride (8) is recycled into the second reactor (9). A reaction liquid (10) is removed from a bottom of the second reactor (9).

Furthermore, the reaction liquid (10) which contains the monochloroester formed in the second reactor (9), and chlorine (11) are introduced into the third reactor (12), and reacted with each other in the presence of a catalyst to form the acid chloride. The reason why the second reactor (9) is placed before the third reactor (12) is that when generated from the aldehyde via the monochloroester, the acid chloride can be obtained in a yield higher than that would be achieved by producing the acid chloride directly from the aldehyde. In particular, since the monochloroester exists in its liquid state within the reaction tube because of its high boiling point, the heat generated from the reaction may be absorbed as the vaporization heat of the monochloroester, and therefore it becomes possible to prevent generation of hot spots. If the acid chloride is generated directly from the aldehyde by no way of the monochloroester, the heat of reaction can not be absorbed by the vaporization heat of any liquid because all of the reactants in the reaction tube will exist in the gas states, and therefore the heat will accumulate to generate hot spots, resulting in significant decrease in selectivity of the reaction.

In order to avoid such disadvantage, it is essential to avoid the accumulation of heat by narrowing the diameter of the reaction tube, and it is also required to use a multi-tubular type reaction tube. By reacting the aldehyde with the acid chloride to form the monochloroester in the second reactor, it became possible to use a single-tubular type reactor, as the third reactor, which is lower in cost than the multi-tubular type and which facilitates the loading and unloading of the catalyst.

The second reactor (9) may be of the single-tubular type, since there is only a little possibility of generation of hot spots because the amount of heat generated by the reaction is small and also because the generated heat is absorbed as the vaporization heat of the liquid constituting the gas-liquid mixed phase in the reactor. A multi-tubular type reactor may also be used as needed.

Although, in FIG. 1, both of the monochloroester (10) and chlorine (11) are introduced into the top of the third reactor (12), that is, they are in parallel flow contact, they may also be arranged in counterflow contact by introducing the monochloroester and chlorine into the top and the bottom of the reactor, respectively.

A reaction gas (13) from the third reactor (12) is removed in its gas state from a lower part of the reactor in the case of parallel flow contact (in the case of counterflow contact, from an upper part of the reactor) and enters the condenser (14). The major constituents of the reaction gas are hydrochloric acid formed during the reaction, unreacted chlorine, and a trace amount of unreacted aldehyde, in addition to the acid chloride. At the condenser (14), hydrochloric acid and chlorine are removed as uncondensed gases (15), and the acid chloride and the unreacted aldehyde are condensed and removed in their liquid states. The reaction liquid (16) comprising the acid chloride and the unreacted aldehyde enters the fourth reactor (17).

In the fourth reactor (17), the aldehyde existing in the acid chloride in a trace amount is reacted with the acid chloride to form the monochloroester, and consequently, the aldehyde concentration is further reduced. Since the difference in boiling point between the acid chloride, which is the final product, and the aldehyde is so small that it is difficult to separate them by rectification, it was required to reduce the aldehyde concentration as low as possible before they enter the following rectifying column. This problem was solved by providing the fourth reactor. The fourth reactor may be of a single-tubular type. The reaction temperature in the fourth reactor is preferably in the range of 20° C.–200° C., more preferably in the range of 80° C.–140° C.

Then, a reaction liquid (18) containing the acid chloride and impurities and exiting from the fourth reactor is introduced into a rectifying column (19) (usually of the batch type). In the rectifying column (19), the reaction liquid (18) containing impurities is purified, and the final product acid chloride (22) is obtained from the column top. A part of the final product acid chloride is recycled into the second reactor (9) for the monochloroester formation. In addition, the monochloroester remaining unreacted in the third reactor (12) and the monochloroester generated in the fourth reactor (17) are removed from the bottoms of the respective columns (not shown), and also recycled into the second reactor. The rectifying column (19) is equipped with a condenser (20) and a reboiler (21). A still residual liquid (23) is retrieved from the reboiler (21).

The acid chlorides obtained according to the present invention are intermediates for pharmaceuticals or agricultural chemicals, and are also used as intermediates for industrial raw materials. For example, ω-hydrododecafluoroheptanoic acid chloride is useful as a stating material for ω-hydrododecafluoroheptanoyl peroxide [H(CF$_2$)$_6$C(=O)O—OC(=O)(CF$_2$)$_6$H] used as a polymerization catalyst.

PREFERRED EMBODIMENTS OF THE INVENTION

The present invention is specifically described below with reference to the following examples, but the present invention is not limited to such examples.

Example 1

Aldehyde Formation

Into a lower part of a distillation column-type reactor (a reaction tube having an internal diameter of 25 mm and a length of 1,000 mm) equipped with a 1,000-cc still and a condenser, 300 cc of activated carbon was charged. Metal heli-coils (5×5×1 mm) were charged above the activated carbon. Into the still, 1,500 g (4.52 mol) of ω-hydrododecafluoroheptanol (alcohol) was introduced, and was brought into total reflux by heating the still (the boiling point of the alcohol is 170° C.). Chlorine gas was introduced at 1.5 L/hr (0.067 mol/hr) and allowed to react. Formed ω-hydrododecafluoroheptanal (aldehyde) and a small amount of low-boiling by-products were drawn out at 22.2 g/hr from a column top of the distillation column. The reaction was conducted for 40 hours and 858.5 g of the reaction product (aldehyde composition) was obtained. According to the result of gas chromatographic analysis, the aldehyde constituted 99 mol % of the products drawn out, and the yield of the aldehyde obtained was 96 mol %.

It was confirmed by the F-NMR spectrum, $^1$H-NMR spectrum and IR absorption spectrum that the product was ω-hydrododecafluoroheptanal having the following formula:

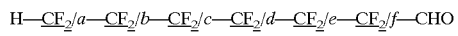

F-NMR (internal standard: CFCl$_3$, 282 MHz) δ ppm
   f. 137.6 ppm [m, 2F, —HCF$_2$]
   d. e. 122.0 ppm [m, 2F, —CF$_2$CHO]
   c. 123.9 ppm [m, 4F, —CF$_2$CF$_2$—]
   b. 125.8 ppm [m, 2F, —CF$_2$]
   a. 129.6 ppm [m, 2F, —CF$_2$]
$^1$H-NMR (internal standard: CDCl$_3$, 300 MHz) δ (ppm) (measured at 40° C.)
   9.56 ppm [t, J=3.3 Hz, 1H, CHO]
   6.08 ppm [tt, J=51.9 Hz, 5.0 Hz, 1H, HCF$_2$—]
IR spectrum (neat)
   2880.1 cm$^{-1}$ (CHO)
   1768.0 cm$^{-1}$ (C=O)

Monochloroester Formation

A vertical reaction tube (internal diameter of the reaction tube: 25 mm, length: 1,000 mm) packed with 300 cc of activated carbon was heated to 120° C. After mixing 335 g of the above aldehyde composition (equivalent to 1 mol of aldehyde) with 364.5 g (1 mol) of ω-hydrododecafluoroheptanoic acid chloride (acid chloride), the mixture was introduced into an upper part of the reaction tube and allowed to react. From the lower part of the reaction tube, 699.5 g of the reaction product was recovered. The composition of the reaction product (monochloroester composition) recovered was 97.5 mol % of monochloroester, 1 mol % of aldehyde, and 1 mol % of acid chloride, according to the result of gas chromatographic analysis. The yield of the monochloroester was 98.5 mol %, because 335 g of the aldehyde composition already contained 1% low-boiling substances.

It was confirmed by the $^{13}$C-NMR spectrum, $^1$H-NMR spectrum and IR absorption spectrum that the product was a monochloroester having the following formula:

$^{13}$C-NMR (internal standard: TMS, 75.469 MHz) δ ppm
   155.7 ppm [t, J=32.2 Hz, 1C, C=O]
   107.8 ppm [tt, J=255.2 Hz, 31.7 Hz, 1C, HCF$_2$—]
   111.6–104.0 ppm [12C, —CF$_2$—]
   78.8 ppm [dd, J=35.7 Hz, 26.3 Hz, 1C, CHCl]
$^1$H-NMR (internal standard: TMS, 300 MHz) δ ppm
   6.88 ppm [dd, J=12.1 Hz, 3.9 Hz, 1H, HCl]
   6.08 ppm [tt, J=51.9.2 Hz, 5.0 Hz, 1H, HCF$_2$—]
IR spectrum (neat)
   1812.8 cm$^{-1}$ (COO)

Acid Chloride Formation

A vertical reaction tube (having internal diameter: 25 mm, length: 1,000 mm) packed with 300 cc of activated carbon was heated to 150° C. The above monochloroester composition was introduced at 34.8 g/hr (equivalent to 0.05 mol-monochloroester/hr) into an upper part of the reaction tube. Chlorine gas was introduced at 4.48 L/hr (0.2 mol/hr) into the upper part in parallel flow with the monochloroester and allowed to react. The reaction was conducted for 10 hours to give 364.2 g of the reaction product. The composition of the reaction product recovered was 97 mol % of acid chloride and 0.6 mol % of aldehyde, according to the result of gas chromatographic analysis. The yield of the acid chloride obtained was 94 mol %.

It was confirmed by the F-NMR spectrum, $^1$H-NMR spectrum and IR absorption spectrum that the product was ω-hydrododecafluoroheptanoic acid chloride.

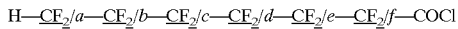

F-NMR (internal standard: C$^{19}$FCl$_3$, 282 MHz) δ ppm
   f. 113.4 ppm [m, 2F, —CF$_2$COCl]
   d. e. 121.7 ppm [m, 4F, —CF$_2$CF$_2$—]
   c. 123.7 ppm [m, 2F, —CF$_2$—]
   b. 129.6 ppm [m, 2F, —CF$_2$—]
   a. 137.6 ppm [m, 2F, —HCF$_2$—]
$^1$H-NMR (internal standard: CDCl$_3$, 300 MHz) δ ppm
   6.08 ppm [tt, J=51.9 Hz, 5.0 Hz, 1H, HCF$_2$—]
IR spectrum (neat)
   1802.8 cm$^{-1}$ (C=O)

Elimination of Aldehyde

Then, a vertical reactor (internal diameter: 8 mm, length: 250 mm) was charged with 5.1 g of activated carbon, and heated to 120° C. in order to conduct a reaction for eliminating the aldehyde from the acid chloride. The acid chloride obtained which contained a small amount of the aldehyde was introduced into an upper part of the reaction tube at 34.2 g/hr, and the reaction product was recovered from the lower part of the reactor. A GC analysis of the reaction product indicated that the aldehyde concentration of the reaction product was 0.03 mol %.

The reaction product (364.2 g) was distilled to give 339 g of distillate containing 99 mol % of acid chloride. The distillation yield of the acid chloride was 95 mol %.

Example 2

Into a distillation column-type reactor (a reaction tube having an internal diameter of 25 mm and a length of 1,000 mm) equipped with a 1,000-cc still and a water-cooled condenser, 300 cc of activated carbon was charged. Metal heli-coils (5×5×1 mm) were charged above the activated carbon. 1,500 g (4.52 mol) of ω-hydrododecafluoroheptanol (alcohol) was introduced into the still, and was brought into total reflux by heating the still (the boiling point of the alcohol is 170° C.). Chlorine gas was introduced at 1.5 L/hr (0.067 mol/hr) and allowed to react. ω-Hydrododecafluoroheptanal (aldehyde) formed and a small amount of low-boiling by-products were drawn out at 22 2 g/hr from the column top of the distillation column. The reaction was conducted for 40 hours, and 858.5 g of the reaction product (aldehyde composition comprising the aldehyde and the low-boiling by-products) was obtained. According to the result of gas chromatographic analysis, the aldehyde constituted 99 mol % of the reaction product drawn out, and the yield of the aldehyde obtained was 96 mol %.

A vertical reaction tube (having internal diameter: 25 mm, length: 1,000 mm) packed with 300 cc of activated carbon was heated to 150° C. The above aldehyde composition was introduced into an upper part of the reaction tube at 33.5 g/hr (equivalent to 0.1 mol-aldehyde/hr). Chlorine gas was introduced at 4.48 L/hr (0.2 mol/hr) into the upper part of the reaction tube in parallel flow with the aldehyde and allowed to react. The reaction was conducted for 10 hours to give 369.3 g of a reaction composition. According to the result of gas chromatographic analysis, ω-hydrododecafluoroheptanoic acid chloride (acid chloride) constituted 78.9 mol % of the product recovered, and the yield of the acid chloride obtained was 80 mol % relative to the conversion of the aldehyde introduced. Accordingly, the calculated overall yield of the acid chloride from the alcohol was 77%.

This composition (369.3 g) was distilled to give 277.0 g of the acid chloride. The distillation yield of the acid chloride was 95 mol %.

Example 3

Into a vertical reaction tube (having internal diameter: 25 mm, length: 1,000 mm) equipped with a heater and packed with 300 cc of activated carbon, ω-hydrododecafluoroheptanol (alcohol) was introduced into an upper part of the reaction tube at 33.2 g/hr (0.1 mol/hr), and chlorine gas was introduced at 6.72 L/hr (0.3 mol/hr) into the upper part of the reaction tube in parallel flow with the alcohol. The reaction was conducted for 10 hours at a reaction temperature of 200° C. The reaction liquid was recovered by condensation to give 363.8 g of an acid chloride composition. According to the result of gas chromatographic analysis, ω-hydrododecafluoroheptanoic acid chloride (acid chloride) constituted 30 mol % of the product recovered, and no starting alcohol remained. The yield of the acid chloride obtained was 30 mol %.

Comparative Example 1

Into a photochlorination apparatus having an internal volume of 500 cc equipped with a high pressure mercury lamp and a water cooler, 332 g of ω-hydrododecafluoroheptanol (alcohol) was introduced, and irradiated with the mercury lamp while retaining the reaction temperature at 20° C. using a water bath. The reaction was conducted for 10 hr by blowing chlorine gas at 4.48 L/hr (0.2 mol/hr) into the liquid. The amount recovered was 330 g, and gas chromatographic analysis of the recovered liquid indicated that the conversion of the alcohol was 70 mol %, and that the selectivity for ω-hydrododecafluoroheptanoic acid chloride (acid chloride) was 9 mol %.

According to the same reaction method and under the same reaction condition, but using carbon tetrachloride as a diluent so that the reaction was conducted with a 10 wt % solution of the alcohol in carbon tetrachloride, the selectivity was found to be the same as that indicated above (9 mol %).

EFFECT OF THE INVENTION

According to the method of the present invention, a higher yield of acid chloride can be achieved. The method of the present invention is suitable for industrially producing an acid chloride.

What is claimed is:

1. A method for producing a monochloroester represented by the formula:

$$R_fCOOCHClR_f$$

wherein $R_f$ is a polyfluoroalkyl group,
the method comprising reacting an aldehyde represented by the formula:

$$R_fCHO$$

wherein $R_f$ is a polyfluoroalkyl group,
with an acid chloride represented by the formula:

$$R_fCOCl$$

wherein $R_f$ is a polyfluoroalkyl group,
in the presence of a catalyst.

2. A method for producing an acid chloride represented by the formula:

$$R_fCOCl$$

wherein $R_f$ is a polyfluoroalkyl group,
the method comprising reacting a monochloroester represented by the formula:

$$R_fCOOCHClR_f$$

wherein $R_f$ is a polyfluoroalkyl group,
with chlorine in the presence of a catalyst.

3. A method for producing an acid chloride represented by the formula:

$$R_fCOCl$$

wherein $R_f$ is a polyfluoroalkyl group,
the method comprising:
(a) a step of reacting a primary alcohol represented by the formula:

$$R_fCH_2OH$$

wherein $R_f$ is a polyfluoroalkyl group
with chlorine in the presence of a catalyst to give an aldehyde represented by the formula:

$$R_fCHO$$

wherein $R_f$ is a polyfluoroalkyl group;
(b) a step of reacting the aldehyde with an acid chloride represented by the formula:

$$R_fCOCl$$

wherein $R_f$ is a polyfluoroalkyl group, in the presence of a catalyst to give a monochloroester represented by the formula:

$R_fCOOCHClR_f$ wherein $R_f$ is a polyfluoroalkyl group; and (c) a step of reacting the monochloroester with chlorine in the presence of a catalyst to give the acid chloride.

4. A method for producing an acid chloride represented by the formula:

$R_fCOCl$ wherein $R_f$ is a polyfluoroalkyl group,
the method comprising:

(a) a step of obtaining an aldehyde having the $R_f$ group by reacting an alcohol represented by the formula:

$R_fCH_2OH$ wherein $R_f$ is a polyfluoroalkyl group,
with chlorine in the presence of a catalyst to give the aldehyde represented by the formula:

$R_fCHO$ wherein $R_f$ is a polyfluoroalkyl group,
in which step the alcohol is brought to reflux in a first reactor filled with the catalyst, and is reacted with chlorine continuously introduced into the reactor, and the aldehyde formed is removed from a column top of the first reactor;

(b) a step of obtaining a monochloroester represented by the formula:

$R_fCOOCHClR_f$ wherein $R_f$ is a polyfluoroalkyl group,
by reacting the aldehyde, in the presence of a catalyst, with an acid chloride represented by the formula:

$R_fCOCl$ wherein $R_f$ is a polyfluoroalkyl group,
in which step the aldehyde and the acid chloride in their liquid states are introduced in parallel flow into a second reactor filled with the catalyst, and the monochloroester is removed in its liquid state;

(c) a step of obtaining the acid chloride by reacting the monochloroester with chlorine in the presence of a catalyst, in which step the monochloroester in its liquid state and chlorine are introduced in parallel flow or in counterflow into a third reactor filled with the catalyst, and a mixture comprising the acid chloride and the aldehyde is removed in its gas state; and (d) a step of eliminating the aldehyde from the mixture comprising the aldehyde and the acid chloride, in which aldehyde-eliminating step the mixture liquid comprising the aldehyde and the acid chloride is introduced into a fourth reactor filled with a catalyst, and the acid chloride is removed in its liquid state.

5. A monochloroester represented by the formula:

$H(CF_2)_6COOCHCl(CF_2)_6H.$

* * * * *